(12) United States Patent
Heigl et al.

(10) Patent No.: US 8,220,994 B2
(45) Date of Patent: Jul. 17, 2012

(54) METHOD FOR CALIBRATING THE POSITION OF A LASER FAN BEAM RELATIVE TO THE PROJECTION GEOMETRY OF AN X-RAY DEVICE AND X-RAY DEVICE

(75) Inventors: Benno Heigl, Coburg (DE); Stefan Lautenschläger, Hausen (DE); Thomas Möller, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 315 days.

(21) Appl. No.: 12/729,449

(22) Filed: Mar. 23, 2010

(65) Prior Publication Data

US 2010/0246778 A1    Sep. 30, 2010

(30) Foreign Application Priority Data

Mar. 24, 2009  (DE) .......................... 10 2009 014 154

(51) Int. Cl.
*G01D 18/00* (2006.01)
(52) U.S. Cl. ...................................................... 378/207
(58) Field of Classification Search ................... 378/62, 378/63, 204–207; 382/154
See application file for complete search history.

(56) References Cited

U.S. PATENT DOCUMENTS

| 5,923,727 | A | 7/1999 | Navab |
| 7,125,165 | B2 | 10/2006 | Luetjens |
| 2008/0107241 | A1 | 5/2008 | Lea |

FOREIGN PATENT DOCUMENTS

| DE | 103 17 137 A1 | 11/2004 |
| DE | 10 2004 048 643 A1 | 4/2006 |
| WO | WO 2008/048921 A2 | 4/2008 |

OTHER PUBLICATIONS

N. Strobel et al., "Improving 3D Image Quality of X-ray C-Arm Imaging Systems by Using Properly Designed Pose Determination Systems for Calibrating the Projection Geometry", Proc. SPIE vol. 5030, 2003, pp. 943-954; Magazine; 2003; US.
Robert Y. Tsai, "An Efficient and Accurate Camera Calibration Technique for 3-D Machine Vision", Proceedings of IEEE Conference on Computer Vision and Pattern Recognition, Miami Beach, FL, 1986, pp. 364-374; Others; 1986.

*Primary Examiner* — Jurie Yun

(57) ABSTRACT

For detecting the relative location of a laser or laser fan beam relative to the x-ray geometry of an x-ray device, a method for calibrating the position of the laser fan beam generated by a laser in relation to the projection geometry of the x-ray device is proposed. The x-ray device comprises an x-ray imaging system featuring an x-ray source and an x-ray detector. The x-ray source, the x-ray detector, the laser, and an imaging facility are arranged on a support. An optical x-ray calibration phantom is used for the calibration. The position of the imaging facility relative to the projection geometry is determined. The position of the laser fan beam relative to the imaging facility is determined. The position of the laser fan beam relative to the projection geometry is reconstructed.

18 Claims, 4 Drawing Sheets

US 8,220,994 B2

METHOD FOR CALIBRATING THE POSITION OF A LASER FAN BEAM RELATIVE TO THE PROJECTION GEOMETRY OF AN X-RAY DEVICE AND X-RAY DEVICE

CROSS REFERENCE TO RELATED APPLICATIONS

This application claims priority of German application No. 10 2009 014 154.5 filed Mar. 24, 2009, which is incorporated by reference herein in its entirety.

FIELD OF THE INVENTION

The invention relates to a method for calibrating the position of at least on laser fan beam generated by a laser relative to the projection geometry of an x-ray device and also to an x-ray device for carrying out a method of this type as claimed in the claims.

BACKGROUND OF THE INVENTION

In new x-ray devices with C-arms adjustable in three dimensions for supporting x-ray imaging systems, as well as the pure x-ray imaging, positioning devices for positioning tools such as puncturing needles by means of laser fan beams generated by lasers are also used. As a result of their construction C-arms twist depending on the angulation selected. These torsions lead to unknown projection geometry and location of the laser positioning device. These devices are needed however in order to determine the location of the tools relative to the images acquired by the x-ray imaging system (2D or 3D) and to use them for positioning. Also, after the x-ray device has been in operation for a long period, the laser fan beams that were originally adjusted when the x-ray device was installed get out of adjustment. In particular vibrations caused by C-arm movements can lead to adjustment problems after long periods of operation.

To determine the x-ray geometry of the x-ray imaging system at the C-arm there are numerous systems known which calculate the projection geometry for a given object, especially a calibration phantom. This calculation is performed in a calibration sequence during the installation of the system in order to use the resulting parameters during operation with patients for 3D reconstruction and 2D/3D fusion. One such method is known for example from the article "Improving 3-D Image Quality of X-ray C-Arm Imaging Systems by Using Properly Designed Pose Determination Systems for Calibrating the Projection Geometry" by N. Strobel, B. Heigl, T. Brunner, O. Schütz, M. Mitschke, K. Wiesent and T. Mertelmeier, Medical Imaging 2003, Physics of Medical Imaging, Proceedings of the SPIE, Volume 5030, Pages 943 ff., 2003. Such a method however does not allow the location of the laser or of the laser fan beam relative to the x-ray geometry to be determined, since the location of a laser fan beam cannot be recorded in the x-ray image.

SUMMARY OF THE INVENTION

The object of the present invention is to provide a method which makes it possible to record the location of the laser or of the laser fan beam relative to the x-ray geometry. Furthermore the object of the invention is to provide an x-ray device suitable for carrying out the method.

The object is inventively achieved by a method for calibrating the position of at least one laser fan beam generated by a laser relative to the projection geometry of an x-ray device and by an x-ray device in accordance with the independent claims. Advantageous embodiments of the invention are the subject matter of the associated dependent claims in each case.

The inventive method for calibrating the position of at least one laser fan beam generated by a laser relative to the projection geometry of an x-ray device, especially using and optical x-ray calibration phantom, with the steps a) Determining the position of the imaging facility relative to the position geometry, b) Determining the position of the laser beam relative to the imaging facility, and c) reconstruction of the position of the laser beam relative to the projection geometry, provide a simple and quick way of enabling possible losses of adjustment of the laser fan beam during the operation of the x-ray device to be corrected. The idea of the invention is for at least one, especially two imaging device(s) arranged on the support of the imaging system to be used in order to establish the relationship between the x-ray geometry and the laser fan beam or beams. The relationship between x-ray geometry and laser fan beam is determined in this case by especially a calibration phantom being able to be imaged both by the imaging facilities and also by the x-ray imaging system.

The method can be carried out during the installation of the x-ray device and at later times automatically with minimal effort. Inaccuracies of the laser or the lasers can be compensated for by taking into account the calculated parameters in the planning and following of the tool positions.

In an advantageous manner an optical x-ray calibration phantom is used for steps a) and/or b). The advantage of such a calibration phantom lies in the fact that its surface, its shape and the x-ray markers contained therein are known and thereby deductions can be made in a simple manner about projection geometries.

According to an embodiment of the invention, step b) is formed from the individual steps of recording at least one image of the calibration phantom irradiated by the laser fan beam by the at least one imaging facility, extraction of the at least one projection line of the at least one laser fan beam on the calibration phantom from the at least one image, determining the three-dimensional location of the at least one projection line relative to the calibration phantom using the surface geometry of the x-ray phantom and the position of the at least one imaging facility relative to the calibration phantom and reconstruction of the plane of the at least one laser fan beam from the at least one 3D projection line. These individual steps represent an especially simple and precise method of determining the position of the laser fan beam relative to the imaging facility.

In accordance with a further embodiment of the invention, step a) is formed by the individual steps of recording at least one image of the calibration phantom by the at least one imaging facility, determining the relative position of the at least one imaging facility in relation to the calibration phantom on the basis of the at least one image, recording of at least one x-ray image of the calibration phantom by the x-ray imaging system, determining the projection geometry of the x-ray imaging system on the basis of the x-ray images and calculating the position of the at least one imaging facility relative to the projection geometry on the basis of the positions determined in relation to the calibration phantom. These individual steps represent a proven method of determining the position of the imaging facility relative to the projection geometry and guarantee with known algorithms a high-quality and precise result.

In accordance with an embodiment of the invention, step b) is formed from the individual steps of recording at least two images of a surface irradiated by the laser fan beam, especially the surface of the patient, by the at least two imaging facilities, extraction of the at least two projection lines of the at least one laser fan beam on the surface of the at least two images, determining the three-dimensional location of the at least two projection lines relative to the surface using the relative positions of the at least two imaging facilities and reconstruction of the plane of the at least one laser fan beam from the at least two 3D projection lines. This has the advantage that even during an x-ray examination of the patient the adjustment of the laser can be checked in that a surface of a patient is used instead of the x-ray phantom for step b). However the calibration phantom and the coordinate system defined by it can continue to be used for step a). Values already determined before the x-ray examination of the patient with a calibration phantom can also be used for step a).

An x-ray device for carrying out the inventive method features a support, an x-ray imaging system featuring an x-ray source and an x-ray detector, at least one laser generating a laser beam, at least one imaging facility, a control unit and a processing unit, with the x-ray source, the x-ray detector, the laser and the at least one imaging facility being arranged on the support. The inventive method in this case is especially suitable for a C-arm x-ray device with a C-arm able to be adjusted in three dimensions which can typically be held on an articulated-arm robot.

In an advantageous manner the at least one imaging facility will be formed by at least one camera, especially by two cameras. Cameras are well-proven and low-cost components with the aid of which, especially when at least two cameras and reconstruction algorithms are used, three-dimensional structures can be created.

Expediently the x-ray device features two lasers for generating two laser fan beams. A laser cross created in this way is especially suitable for positioning instruments such as puncturing needles for example with high precision.

In accordance with a further embodiment of the invention the at least one imaging facility and/or the at least one laser are arranged on the x-ray detector. Such an arrangement is advantageous for the laser or the lasers in order to guarantee an alignment of the laser fan beam on an instrument which is as unrestricted as possible. As a consequence of this it is also advantageous for the imaging facility or facilities to be able to record the laser fan beam or its projection line(s) on an x-ray phantom directly and without hindrance. If two or more imaging facilities are present, it is advantageous for a good three-dimensional representation to arrange the different imaging facilities at different positions, especially as far away from each other as possible. Both imaging facilities and also lasers are especially arranged on the housing of the x-ray detector.

Expediently the x-ray device features a system controller for controlling x-ray imaging, imaging, movements and other functions as well as a display system for image processing and image display.

In accordance with a further embodiment of the invention the calibration phantom used features both structures visible to x-rays and also optically visible structures; its structure and surface geometry are known to the x-ray device.

BRIEF DESCRIPTION OF THE DRAWINGS

The invention as well as a further advantageous embodiment in accordance with features of the dependent claims will be explained in greater detail below on the basis of schematic diagrams of exemplary embodiments in the drawing, without the invention being restricted to these exemplary embodiments in any way. The figures show:

DETAILED DESCRIPTION OF THE INVENTION

Figure 1:
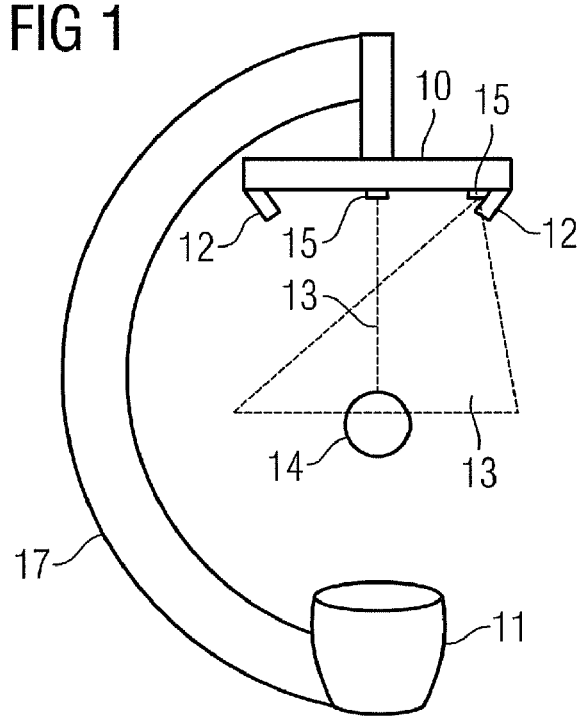
FIG. 1 a view of a recording system of an x-ray device with two imaging facilities and two lasers, FIG. 2 an enlarged view of an x-ray detector with two imaging facilities and two lasers in accordance with FIG. 1, FIG. 3 a typical calibration phantom for calibrating the x-ray geometry, FIG. 4 a flowchart of the inventive method, FIG. 5 a flowchart of the inventive method with individual steps, FIG. 6 an x-ray image of the calibration phantom in accordance with FIG. 3, FIG. 7 an optical image of the calibration phantom in accordance with FIG. 3, FIG. 8 a view of the calibration phantom irradiated by a laser fan beam and FIG. 9 an optical image of the calibration phantom in accordance with FIG. 3 with a projection line of a laser fan beam.
Figure 2:
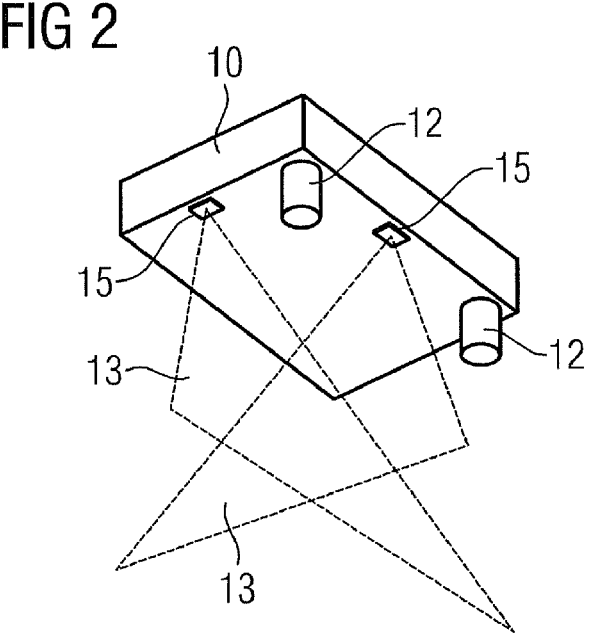

Sections of the inventive x-ray device are shown in FIG. 1 and FIG. 2, in which an x-ray detector 10 and an x-ray source 11 are arranged on an adjustable, movable 17. The C-arm 17 is preferably adjustable in three dimensions, for example in that it is attached to a multi-axis articulated-arm robot. Arranged on the x-ray detector are two lasers 15 embodied as positioning facilities for instruments, which each generate a laser fan beam 13 along the beam direction of the x-ray beam. The laser fan beans form a laser cross for instrument positioning. The positioning of instruments by means of laser fan beams and laser crosses is known. In addition two cameras 12 are arranged on the x-ray detector 10 which are aligned in the direction of the laser fan beams. Ideally the cameras 12 are arranged at different ends of the x-ray detector 10 in order to be able to reconstruct 3D structures as well as possible with the largest possible spacing. The inventive method can however also be carried out with one or with more than two cameras 12. For the control of the x-ray system, i.e. of the x-ray detector, the x-ray source, the cameras, the lasers and the other components for example, a system controller can typically be provided. The system controller can control the inventive method automatically. Computation or processing units can be provided for calculations and reconstructions; memory units can be provided for storage of data and information.

A calibration phantom suitable for the inventive method features both x-ray-absorbing markers and also structures visible in the camera image. In addition the relative location of the structures in relation to a coordinate system assigned to the calibration phantom and the surface geometry of the calibration phantom is known and both can be included in the calculations.

Figure 3:
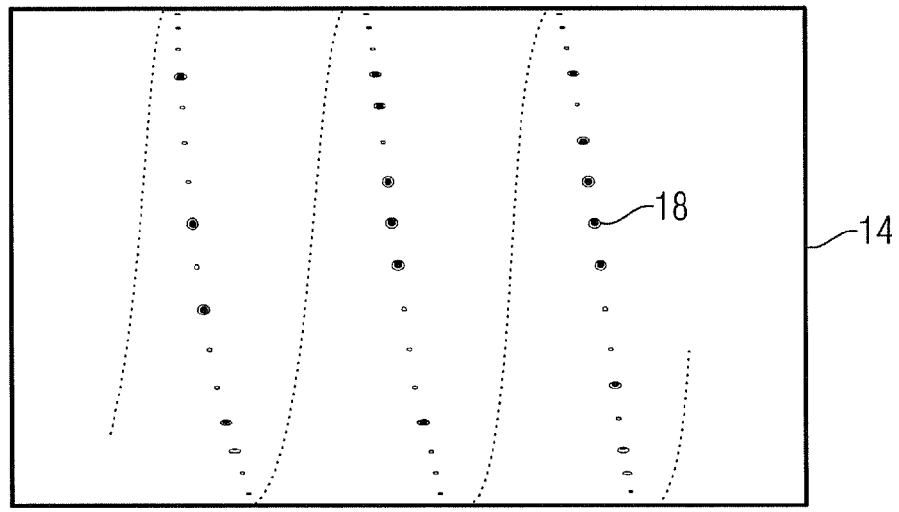
Figure 6:
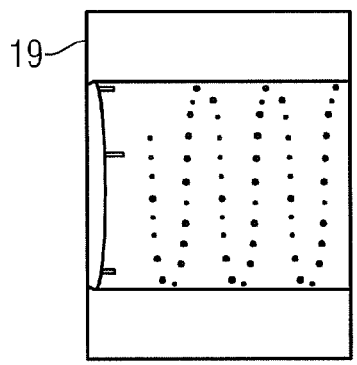
Figure 7:
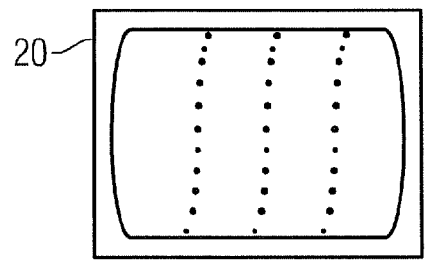

An example of such a calibration phantom 14 is shown in FIG. 3. The calibration phantom 14 consists of a plastic cylinder transparent to x-rays into which 108 balls 18 are recessed. The balls consist of stainless steel and thus act as markers in the x-ray images. The balls are arranged in the shape of a helix. The helix-shape of marker arrangement has the advantage that, especially with circular scanning paths, as are usual with x-ray C-arms, sinusoidal curves are detectable in the projection images, i.e. the greatest possible number of markers are imaged in the optimum way simultaneously. The balls 18 of the calibration phantom can have two different sizes. The selection between large and small ball for a specific location in the helix is made by an encoding, with a binary encoding being produced by the option of providing two different sizes of ball. The encoding is selected so that a part sequence of eight balls in the image is sufficient if their different sizes can be recognized in the projection image in order to precisely allocate which eight balls of the 108 balls are being mapped in the projection image. An example for an x-ray image 19 of the calibration phantom is shown in FIG. 6 and an example for a camera image 20 of the calibration phantom is shown in FIG. 7.

Figure 4:
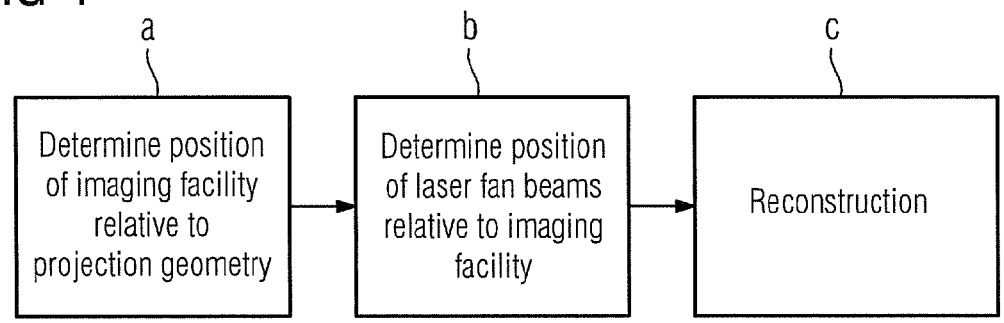
Figure 5:
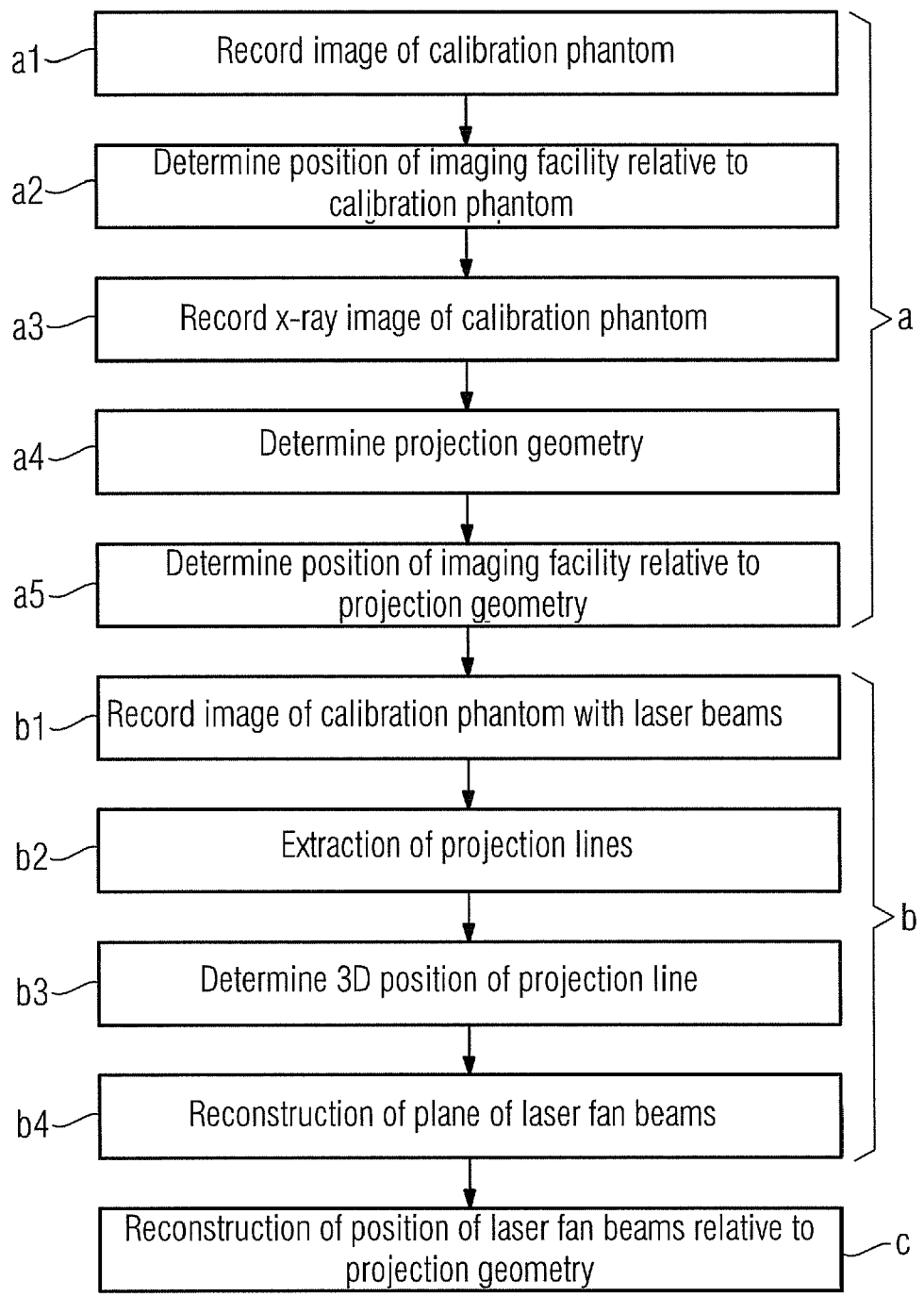

FIG. 4 gives an overview of the inventive method, with the position of the imaging facility relative to the projection geometry of the x-ray imaging system (x-ray detector and x-ray source) being determined (step a)), then the position of the laser beam relative to the imaging facility being determined (step b)) and subsequently the position of the laser beam relative to the projection geometry being reconstructed (step c)). FIG. 5 shows the individual steps of the method.

By means of the following individual steps the position of the imaging facility(facilities) relative to the x-ray geometry is determined using the calibration phantom 14 for an angulation of the Through known methods, as are known from the example from the publication in title "Improving 3-D Image Quality of X-ray C-Arm Imaging Systems by Using Properly Designed Pose Determination Systems for Calibrating the Projection Geometry" already mentioned, after recording at least one x-ray image of the calibration phantom (step a1) the projection geometry of the x-ray imaging system is determined by means of the x-ray-absorbing markers of the calibration phantom from an x-ray image of the calibration phantom (step a2). Likewise in a known manner, for example from the publication "An Efficient and Accurate Camera Calibration Technique for 3-D machine vision" by R. Y. Tsay, Proceedings of IEEE Conference on Computer Vision and Pattern Recognition, Miami Beach, Fla., Pages 364 to 374, 1986, after at least one image of the calibration phantom has been recorded (step a3) the relative position of the imaging facility (facilities) in relation to the calibration phantom is determined from the image or the images of the imaging facilities (step a4).

There can also be provision for carrying out the steps a3 and a4 before the steps a1 and a2). The fact that the positions of the x-ray geometry and of the imaging facility(facilities) are now able to be calculated in relation to the same coordinate system, i.e. that of the calibration phantom, means that all relative positions between the imaging facility(facilities) and the x-ray geometry are also able to be calculated (step a5). Step a or the individual steps a1 to a5 respectively do not have to be calculated again for each angulation, instead the relative position determined once between the x-ray geometry and the imaging facility(facilities) can be stored and used again.

Figure 8:
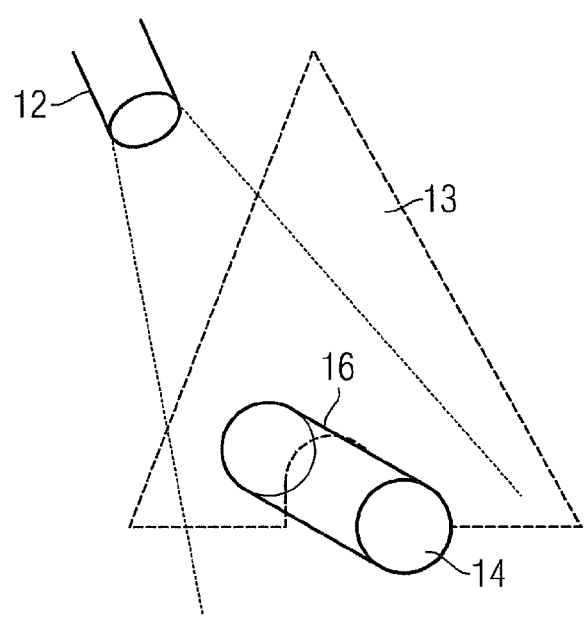
Figure 9:
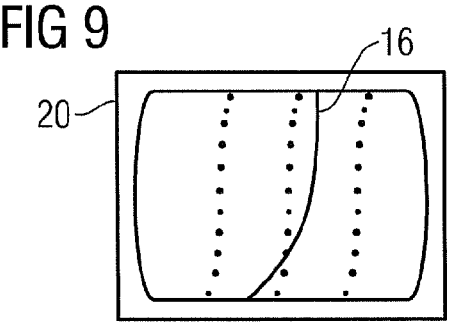

In order to now determine the position of the laser or of the laser fan beams in relation to the imaging facility, for example during an installation of the x-ray device, the following individual steps are to be carried out. Firstly one or more images of the calibration phantom illuminated by the laser fan beam are recorded by means of the at least one imaging facility (step b1)). The control can for example be taken over by the system controller of the x-ray device. FIG. 8 shows how the calibration phantom 14 is illuminated by a laser fan beam 13 and a projection line 16 forms accordingly on the calibration phantom. FIG. 9 shows such an image 20 with the mapped two-dimensional projection line. Subsequently the at least one projection line 16 of the at least one laser fan beam 13 on the calibration phantom is extracted from the at least one image (step b2)). This can be done by means of an image processing facility and software for example.

From the mapping of the two-dimensional projection line the three-dimensional position of the protection line is subsequently determined relative to the calibration phantom (step b3)). The known surface geometry of the calibration phantom and the relative position of the imaging facility in relation to the calibration phantom are included for this purpose. With the aid of this information the three-dimensional position of the projection line can be calculated with software typically by means of an image processing unit or a computation unit. From the three-dimensional projection line the plane of the laser fan beam and/or the position of the laser can then be reconstructed in a simple manner (step b4)). In the case of a number of imaging facilities, a number of images are recorded accordingly and the projection lines are determined and the laser fan beam or the laser fan beams are reconstructed from these. If a number, e.g. two laser fan beams, are present, the two planes are determined separately from one another. The crossing point can then be determined from these.

Subsequently the laser fan beam or its plane are then reconstructed relative to the x-ray geometry (step c)). All the determination or reconstruction steps can be computed by means of image processing or computation units and software with the corresponding algorithms.

The inventive method is carried out for any given angulations, i.e. positions of the C-arm. The information obtained from this can then be used in the position planning and position tracing of tools during an operation, an x-ray examination or an interventional procedure, in order to compensate for system-specific inaccuracies.

To limit the number of angulations of the C-arm to be calibrated, a discreet undersampling can take place and the correction parameters for intei mediate positions can be determined by means of interpolation. As well as interpolation a model-based approach and the estimation of parameters from the acquired and computed checkpoints is also possible.

In order to solve the problem of the possible changes in adjustment of the laser or of the lasers over time, if at least two imaging facilities are present, the exact geometry of the laser or of the laser fan beam relative to the imaging facilities can also be determined by the following individual steps. In each case at least one image of a surface, for example the surface of a patient, is recorded by at least two imaging facilities (step b5)), for example under the control of the system controller. Subsequently the respective projection lines of the at least one laser fan beam 13 on the surface of the at least two images are extracted (step b6)). This can once again be undertaken automatically. Subsequently the three-dimensional position of the projection lines is determined from the images (step b7)), with the known position of the imaging facilities relative to the coordinate system after step a) which was determined in the first step by the calibration phantom, being used. Subsequently the plane of the laser fan beam is reconstructed on the basis of the reconstructed three-dimensional locations of the projection lines (step b8)). Subsequently the laser fan beam or its plane are reconstructed again relative to the x-ray geometry (step c)).

The idea of the invention lies in imaging facilities attached to the for example video cameras, being used to establish the relationship between x-ray geometry and laser. The structure of the corresponding x-ray device typically features a movable C-arm, a laser positioning device mounted on the C-arm, typically in the form of two laser fan beam projectors mounted on the housing of the x-ray detector, and one or more video cameras mounted on the C-arm, for example directly on the housing of the x-ray detector. The cameras are aligned in the direction of the laser beams.

In a calibration method the relationship between x-ray geometry and laser fan beams can be determined by an image of a calibration phantom being recorded both by the video cameras and also by the x-ray imaging system. Advantageously the calibration phantom features both x-ray-absorbing markers and also structures visible in the camera image, the relative position of the structures is known in relation to a coordinate system assigned to the calibration phantom and the surface geometry of the x-ray phantom is known and likewise described in the above-mentioned coordinate system.

For a C-arm angulation the location of the video cameras relative to the x-ray geometry can be determined by the projection geometry of the x-ray imaging system being determined by means of the x-ray-absorbing marker from an x-ray image of the calibration phantom by known methods, the relative position of the video cameras in relation to the calibration phantom can be determined from video images of the camera(s) by known methods and all relative locations between the video cameras and the x-ray geometry can be computed from the now computable locations of the x-ray geometry and of the video cameras in relation to the same coordinate system.

The location of the laser relative to the x-ray geometry is calculated for example during an installation, by video images being recorded with the laser positioning device switched on, the laser projection on the calibration phantom being automatically extracted in the recorded video images, the 3D location of the projection lines in the coordinate system of the calibration phantom being determined using the known surface geometry and the relative location of the video cameras in relation to the same coordinate system (this is possible with at least one camera) and the alignment of the planes described by the laser fan beams being reconstructed from the projection lines.

In order to be able to follow changes in the laser adjustments after the installation of the x-ray device, if there are at least two video cameras present, the exact laser geometry relative to the C-arm can be determined via video images from at least two cameras being recorded during the patient procedure, the lines generated by projection of the laser fan beams on the patient's surface are extracted from the video images, the 3D line is reconstructed from the individual 2D lines of the video images using the known locations of the video cameras relative to the coordinate system which was determined in the first step by the calibration phantom and the alignment of the planes described by the laser fan beams is computed from the reconstructed 3D lines.

The invention can be briefly summarized as follows: To record the location of a laser or laser fan beam relative to the x-ray geometry of an x-ray device a method is provided for calibrating the position of at least one laser fan beam generated by a laser relative to the projection geometry of an x-ray device with an x-ray recording system featuring an x-ray source and an x-ray detector, with the x-ray source, the x-ray detector, the laser and at least one imaging facility being arranged on a support, with the following steps:
a) Determining the position of the imaging facility relative to the projection geometry,
b) Determining the position of the laser fan beam relative to the imaging facility and
c) Reconstruction of the position of the laser fan beam relative to the projection geometry.

The invention claimed is:
1. A method for calibrating a position of a laser fan beam generated by a laser relative to a projection geometry of an x-ray device having an x-ray image system and an imaging device, comprising:
   determining a position of the imaging device relative to the projection geometry;
   determining a position of the laser fan beam relative to the imaging device; and
   reconstructing the position of the laser fan beam relative to the projection geometry.

2. The method as claimed in claim 1, wherein the position of the imaging device relative to the projection geometry and the position of the laser fan beam relative to the imaging device are determined by an optical x-ray calibration phantom.

3. The method as claimed in claim 2, wherein the position of the imaging device relative to the projection geometry is determined by:
   recording an image of the calibration phantom by the imaging device;
   determining a position of the imaging device relative to the calibration phantom based on the image;
   recording an x-ray image of the calibration phantom by the x-ray imaging system;
   determining a position of the projection geometry of the x-ray imaging system relative to the calibration phantom based on the x-ray image; and
   calculating the position of the imaging device relative to the projection geometry based on the position of the imaging device relative to the calibration phantom.

4. The method as claimed in claim 2, wherein the position of the laser fan beam relative to the imaging device is determined by:
   recording an image of the calibration phantom illuminated by the laser fan beam by the imaging device;
   extracting a projection line of the laser fan beam on the calibration phantom from the image;
   determining a three-dimensional location of the projection line relative to the calibration phantom using a surface geometry of the x-ray phantom and a position of the imaging device relative to the calibration phantom from the image; and
   reconstructing a plane of the laser fan beam from the three-dimensional location of the projection line.

5. The method as claimed in claim 2, wherein the position of the laser fan beam relative to the imaging device is determined by:
   recording two images of the calibration phantom illuminated by the laser fan beam by the imaging device and a second image device respectively;
   extracting a projection line of the laser fan beam on the surface from the two images;
   determining a three-dimensional location of the projection line relative to the calibration phantom using a surface geometry of the x-ray phantom and positions of the imaging device and the second image device relative to the calibration phantom from the images; and
   reconstructing a plane of the laser fan beam from the three-dimensional location of the projection line.

6. The method as claimed in claim 2, wherein the calibration phantom is a surface of a patient.

7. The method as claimed in claim 1, wherein the laser, the imaging device, and an x-ray source and an x-ray detector of the x-ray imaging system are arranged on a support.

8. The method as claimed in claim 7, wherein the support is a C-arm.

9. The method as claimed in claim 7, wherein a plurality of imaging devices are arranged on the support.

10. An x-ray device, comprising:
an x-ray imaging system comprising an x-ray source and an x-ray detector that records an x-ray image of an object;
a laser that generates a laser fan beam for illuminating the object;
an imaging device that records an image of the object; and
a computation unit that:
- determines a position of the imaging device relative to a projection geometry of the x-ray device;
- determines a position of the laser fan beam relative to the imaging device; and
- calibrates a position of the laser fan beam relative to the projection geometry by reconstructing the position of the laser fan beam relative to the projection geometry.

11. The x-ray device as claimed in claim 10, wherein the x-ray source, the x-ray detector, the laser, and the imaging device are arranged on a support.

12. The x-ray device as claimed in claim 11, wherein the support is a C-arm and is able to be adjusted in three dimensions.

13. The x-ray device as claimed in claim 10, wherein the imaging device comprises a camera.

14. The x-ray device as claimed in claim 10, further comprising a second laser that generates a second laser fan beam for generating a laser cross with the laser fan beam.

15. The x-ray device as claimed in claim 10, wherein the imaging device or the laser is arranged on the x-ray detector.

16. The x-ray device as claimed in claim 10, wherein the object is a calibration phantom.

17. The x-ray device as claimed in claim 16, wherein the calibration phantom comprises a structure that is both x-ray-visible and optically visible.

18. The x-ray device as claimed in claim 16, wherein the calibration phantom comprises a known structure of a surface geometry.

* * * * *